United States Patent
Glover et al.

(10) Patent No.: US 6,406,856 B1
(45) Date of Patent: Jun. 18, 2002

(54) BIOSENSOR

(75) Inventors: Lesley Anne Glover, Inverurie; Roger Paul Hollis, Muckhart; Kenneth Stuart Killham, Inverurie, all of (GB)

(73) Assignee: Aberdeen University, Aberdeen (GB)

( * ) Notice: Subject to any disclaimer, the term of this patent is extended or adjusted under 35 U.S.C. 154(b) by 0 days.

(21) Appl. No.: 09/786,846

(22) PCT Filed: Sep. 9, 1999

(86) PCT No.: PCT/GB99/02997

§ 371 (c)(1),
(2), (4) Date: Mar. 9, 2001

(87) PCT Pub. No.: WO00/14267

PCT Pub. Date: Mar. 16, 2000

(30) Foreign Application Priority Data

Sep. 9, 1998 (GB) ............................................. 9819666

(51) Int. Cl.⁷ ................................................. C12Q 1/68
(52) U.S. Cl. ........................ 435/6; 435/189; 435/254.2; 435/254.21

(58) Field of Search ......................... 435/6, 189, 254.2, 435/254.21

(56) References Cited

U.S. PATENT DOCUMENTS 5,665,543 A    9/1997   Foulkes et al.

FOREIGN PATENT DOCUMENTS

| GB | 2203209 | 2/1997 |
| WO | WO 93/03179 | 2/1993 |
| WO | WO 98/04716 | 2/1998 |

*Primary Examiner*—James Ketter
(74) *Attorney, Agent, or Firm*—Nixon Peabody LLP

(57) ABSTRACT

The present invention relates to a method for evaluating biological effects in a substance which method comprises sampling the substance, subjecting the sample to an assay in the presence of a biosensor engineered with a gene which expresses a light emitting protein and noting the light output; characterized in that the biosensor is eukaryotic and the substance is assayable over any pH between pH1 and pH12. Such a eukaryotic sensor may be derived from *Saccharomyces cerevisiae* and is useful in assaying potable waters.

29 Claims, 15 Drawing Sheets

Primer S5R

5'-GTGTTGCTTTCTTATCCGCGGAGAAATAAATTGAAT-3'

Primer S3R

5'-TTTTTCGAAACGCAGAGCTCTCGAGTTATTAAACTT-3'

Primer X5R

5'-CGTAATACCAACAAATCTAGAAATGTTATGAAATTT-3'

Primer N3R

5'-AAGGGGCATCGCGGCCGCTTCAGCATCAGTTAAACG-3'

Primer B5RL

5'-TTTGCAAAAAGCTTGGGATCCCGGTACTGTTGGTAA-3'

Primer N3RL

5'-TAGCTAAGAATTTCGCGGCCGCTGAATACAGTTACA-3'

Primer 5LEADL

5'-ACAGATCACCGGATCCATCAAGACACCAATCAAAACAAATAAAACATCATCACAATGGAAGACGCCAAAAACATAAAGAAAGGCCCG-3'

Primer N3RD

5'-TCTAGAGCGGCCGCTGAATACAGTTACATTTTACTTTCCGCCCTTCTTGGCCTTT-3'

*Fig. 2a*

PRIMER ST1K1

5' - GAGCTCTGCGTTTCGAAAAACCGGAGACGGTCACAGCTT-3'

PRIMER rLUC

5' -AGCCTCATAAATAAAGGTAGATAGTAAAGTATACAAGAGAAGAATCCCAAGAT
GGAAGACGCCAAAAACATAAAGAAAGGCCCG -3'

PRIMER rURA

5' - ATCAAACATCATTCTGCAGAACTGAAAACATACTTGAACACTTGGGACAGCTG
ACCTGATGCGGTATTTTCTCCTTACGCATCT -3'

PRIMER mrL

5' - AGCCTCATAAATAAAGGT -3'

PRIMER mrU

5' - TTTTCTCCTTACGCATCT -3'

*Fig. 2b*

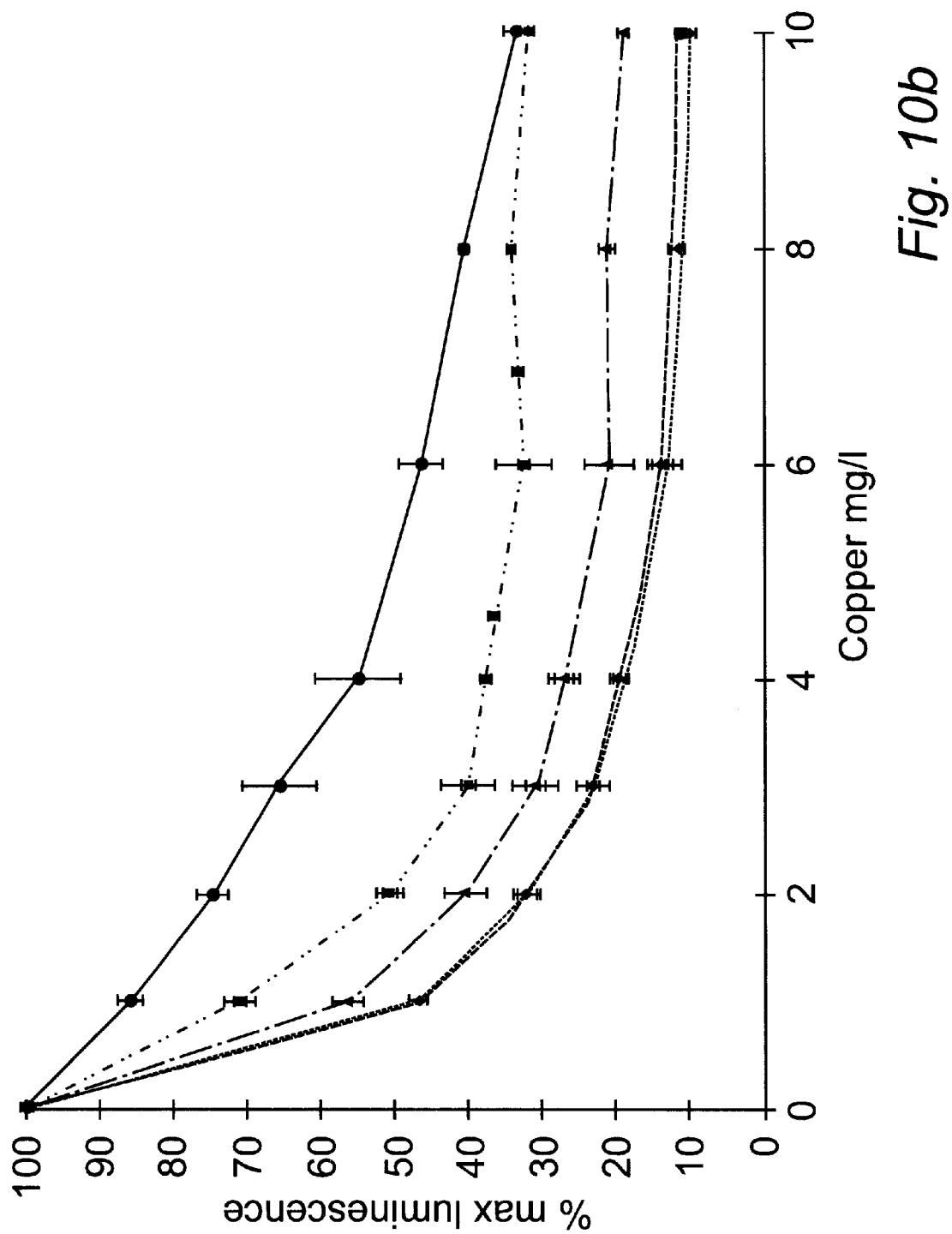

BIOSENSOR

The present invention relates to a eukaryotic biosensor for the detection of xenobiotics and bioactive compounds. It will be appreciated that xenobiotics are not necessarily bioactive.

The problems of environmental contamination with toxic chemicals are becoming increasingly apparent. Such pollution has fuelled the need to develop novel, rapid and inexpensive methods for toxin detection in the environment.

Assay systems such as High-Performance Liquid Chromatography accurately predict quantities of chemical components but will not indicate toxicity or bioavailability (potential of compound to react with cellular components).

Prokaryotic biosensors, for example MICROTOX®, were created to indicate the toxicity and bioavailability of chemical components. Prokaryotic biosensors are unicellular living organisms that provide information about in vivo toxicity rapidly and reliably. They can detect a wide range of pollutants within a certain narrow pH range, whilst simultaneously assessing bioavailability in environmental samples. However, the MICROTOX® biosensors are generally not sensitive to eukaryotic-specific molecules, such as DIURON® 3-(3,4-dichlorophenyl)-1,1-dimethylurea, and they only operate within a narrow pH range.

Existing assays for quantifying in vivo toxicity of chemicals for eukaryotic cells exploit whole animal models or tissue culture, which is both time consuming and expensive. The unicellular yeast *Saccharomyces cerevisiae* has previously been shown to function as a biosensor using BOD (Biochemical Oxygen Demand) respirometry. However, this BOD assay system is also time consuming and expensive.

The usual method for selecting plasmids or episomes which have undergone bioengineering is that during the genetic engineering procedure antibiotic resistance genes are transferred in the vector with the desired gene. Therefore when the transfer is successful the plasmid and therefore the host cell is resistant to antibiotics. The bioengineered cells can then be selected by growing them in the presence of antibiotics. However, antibiotic resistance is becoming more and more of a problem. There are now 'Superbugs' which cannot be treated by antibiotics and many other bacteria are resistant to all but one antibiotic. Now there is a concerted effort on the part of scientists to reduce the number of antibiotic resistence genes that they transfer from one microorganism to another.

One object of the present invention is to develop a cheap and quick assay for quantifying the in vivo toxicity of chemical components for eukaryotic cells which will operate over a wide pH range and function in the presence of an organic solvent.

Another object of the present invention is to develop a cheap and quick assay for quantifying the in vivo toxicity of chemical components for eukaryotic cells through chromosomal integration of the luciferase gene without the transfer of antibiotic resistance.

According to a first aspect of the invention there is provided a method for evaluating a biological effect of a substance, the method comprising the following steps:

a) preparing a eukaryotic biosensor engineered with a gene which constitutively expresses a light emitting protein;

b) sampling the substance;

c) subjecting the sampled substance at any pH between pH1 and pH12 to an assay in the presence of the biosensor; and d) monitoring any changes in light output.

It should be noted that the term "biological effects" include all toxicity testing and the steps in the above identified method can be carried out in any order. In addition, a substance can be taken to be, inter alia, a liquid, such as water, a solid or suspension or colloid or sediment or sludge.

Typically biosensors have been produced from prokaryotic cells which can only operate in a narrow pH range. The inventive eukaryotic biosensor can function at any pH between pH1 and pH12 which makes it more useful for environmental samples and commercially viable. The biosensor is cheap and easy to produce so it can be used in mass and routine screening of water supplies. The pH tolerance of the yeast biosensor for example will enable toxicity assessment of industrial waste and toxicity in extreme environmental samples such as acid mining waste.

In a preferred embodiment the eukaryotic biosensor of the invention is derived from the Saccharomyces genus and preferably from *Saccharomyces cerevisiae*. *S. cerevisiae* is an ideal cell to function as a biosensor because it can tolerate an external pH within the range pH1 and pH12 and it is permeable to many xenobiotics and bioactive compounds. It also senses the toxic effect of the contaminated liquids on eukaryotic cells and therefore more accurately indicates the liquid samples possible toxicity to higher order organisms, and particularly to mammals.

Conveniently the light emitting protein is a luciferase.

In a preferred embodiment the luciferase is either a bacterial luciferase or a eukaryotic luciferase. Preferably the bacterial luciferase is from *Vibrio harveyi* and the eukaryotic luciferase is a firefly luciferase from *Photinus pyralis*. Both the luciferases require an exogenous addition of the substrate n-decyl aldehyde and luciferin, respectively. The luciferin is an amphipathic molecule that has a carboxyl group charged at physiological pH which prevents its free passage across cell membranes. This problem is overcome by acidifying the sample containing the cells and the biosensor after exposure to the potentially toxic sample. It is therefore important that these cells can remain metabolically active at an acidic pH. Both these luciferase genes produce light emitting proteins that require energy from the eukaryotic cell to produce light and therefore the level of light output is dependant on the health of the cell. Thus if the cell viability is challenged by components of the sample, for example due to the presence of a toxin, the level of light will fall and the resultant toxic effect of the sample can be noted.

The substance may be contaminated with a xenobiotic compound or a bioactive compound. For example, a xenobiotic compound may be selected from copper, 3,5-dichlorophenol, 2,4-dichlorophenol, MECOPROP® (±)-2-(4-chloro-0-tolyloxy) propionic acid, DIURON®, paralytic shell fish toxins, benzo (a) pyrene and MCPA. Copper, 3,5-dichlorophenol and 2,4-dichlorophenol are compounds found in industrial waste, which can find their way into rivers and lakes through accidental or deliberate dumping. They can also leach out of the soil around industrial waste plants. They are toxic to river dwelling organisms and those higher up the food chain. Accordingly, their levels in river water must be carefully monitored. MECOPROP® and DIURON® are herbicides which are used liberally by farmers. They leach out of the soil into rivers where once again they and their biologically active derivatives are toxic to the river dwelling organisms and those higher up the food chain.

Organic solvents such as ethanol, methanol, acetone and DMSO are also harmful to organisms. The biosensor herein described in stable in an environment which contains such organic solvents and it can therefore be used to identify substances which are being tested for toxicity to higher organisms, in the presence of these solvents. It will be appreciated that the presence of these solvents thus does not detract from the assay of the substances.

In a second aspect of the invention there is provided a biosensor comprising a bioengineered organism from the Saccharomyces genus expressing a light emitting protein gene wherein the level of light emitted by the organisms is dependent on the environmental conditions surrounding the organism. A gene conferring antibiotic resistance is not necessarily required for biosensor selection. The light emitting protein gene may be present on a plasmid which has been transferred into Saccharomyces species.

In a third aspect of the invention there is provided a biosensor comprising a eukaryotic bioengineered organism with a chromosomally integrated gene fragment expressing a light emitting protein wherein the level of light emitted by the organisms is dependent on the environmental conditions surrounding the organism. Preferably the Eukaryotic biosensor is adapted for cell division during assay.

A specific embodiment of this invention is a eukaryotic biosensor S. cerevisiae LUCΔ deposited at the National Collection of Industrial and Marine Bacteria at Aberdeen University, 23 St Machar Drive, Aberdeen, UK on the Aug. 28, 1998 under the number NCIMB 40969.

This invention will now be described, by illustration only, with reference to the following examples and the accompanying figures.

FIG. 2a shows the genetic code of primers used in PCR for the construction of the biosensor plasmid of FIG. 1b.

FIG. 2b shows the genetic code of primers used in a PCR for the construction of the integrative luciferase cassette.

----O---- and the mean OD 600 nm (Optical Density)

——•—— are shown.

Figure 4:
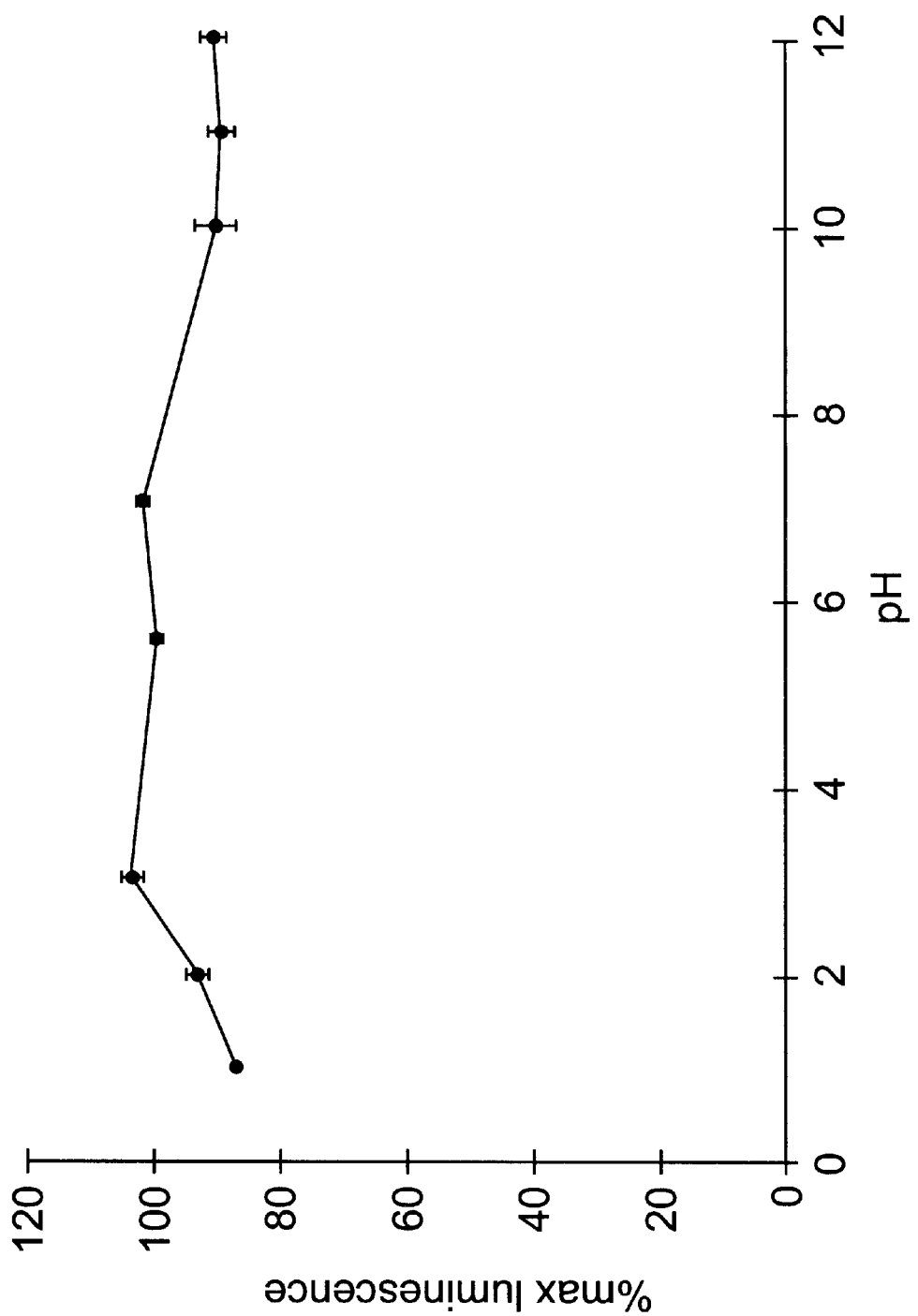

FIG. 4 is a graphical representation of the effect of pH on the luminescence of the S. cerevisiae pPLUCΔP biosensor. The graph shows the mean luminescence.

Figure 5:
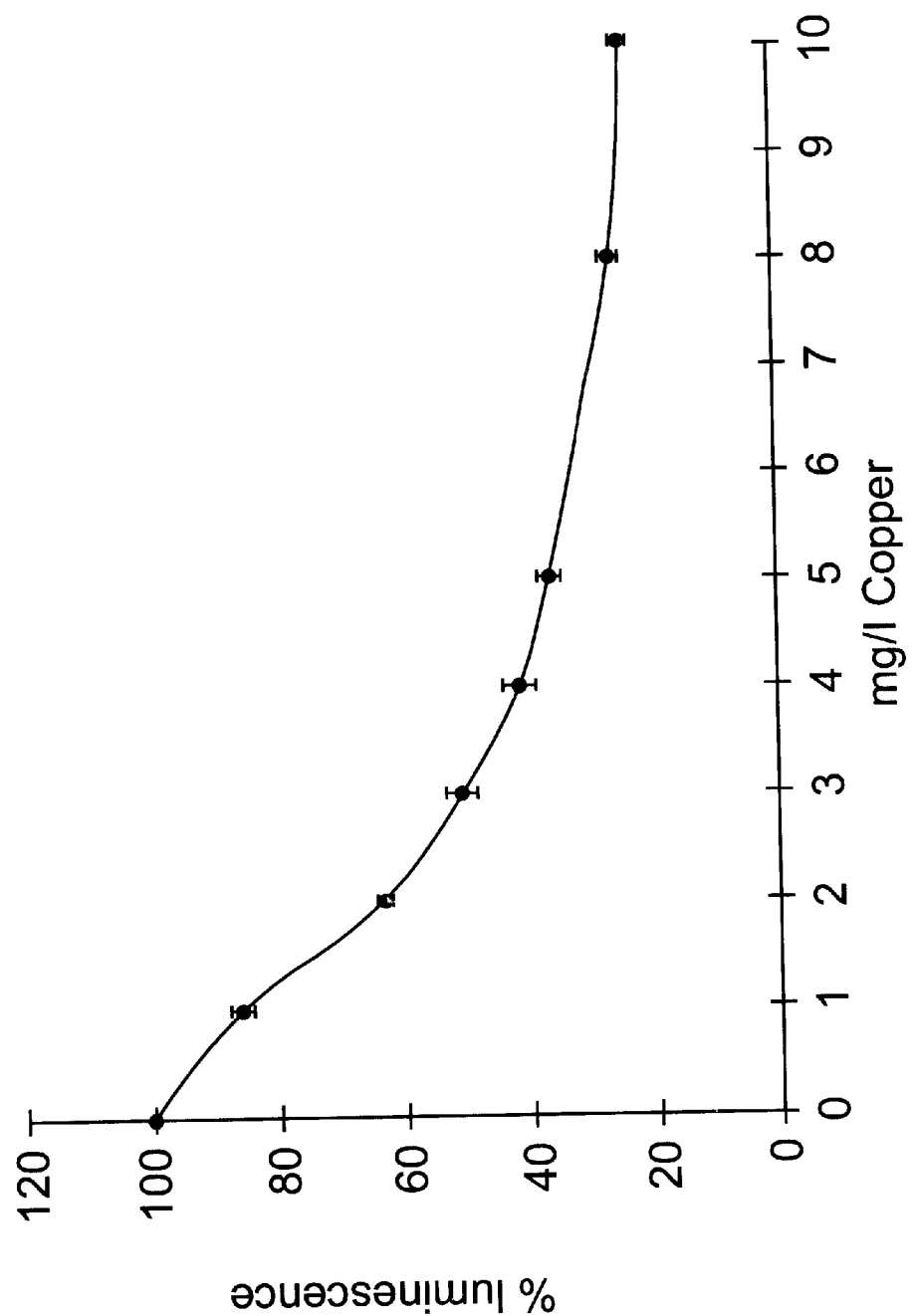

FIG. 5 is a graphical representation of the luminescence of the S. cerevisiae pPLUCΔP biosensor 10 minutes after exposure to a range of copper concentrations.

Figure 6:
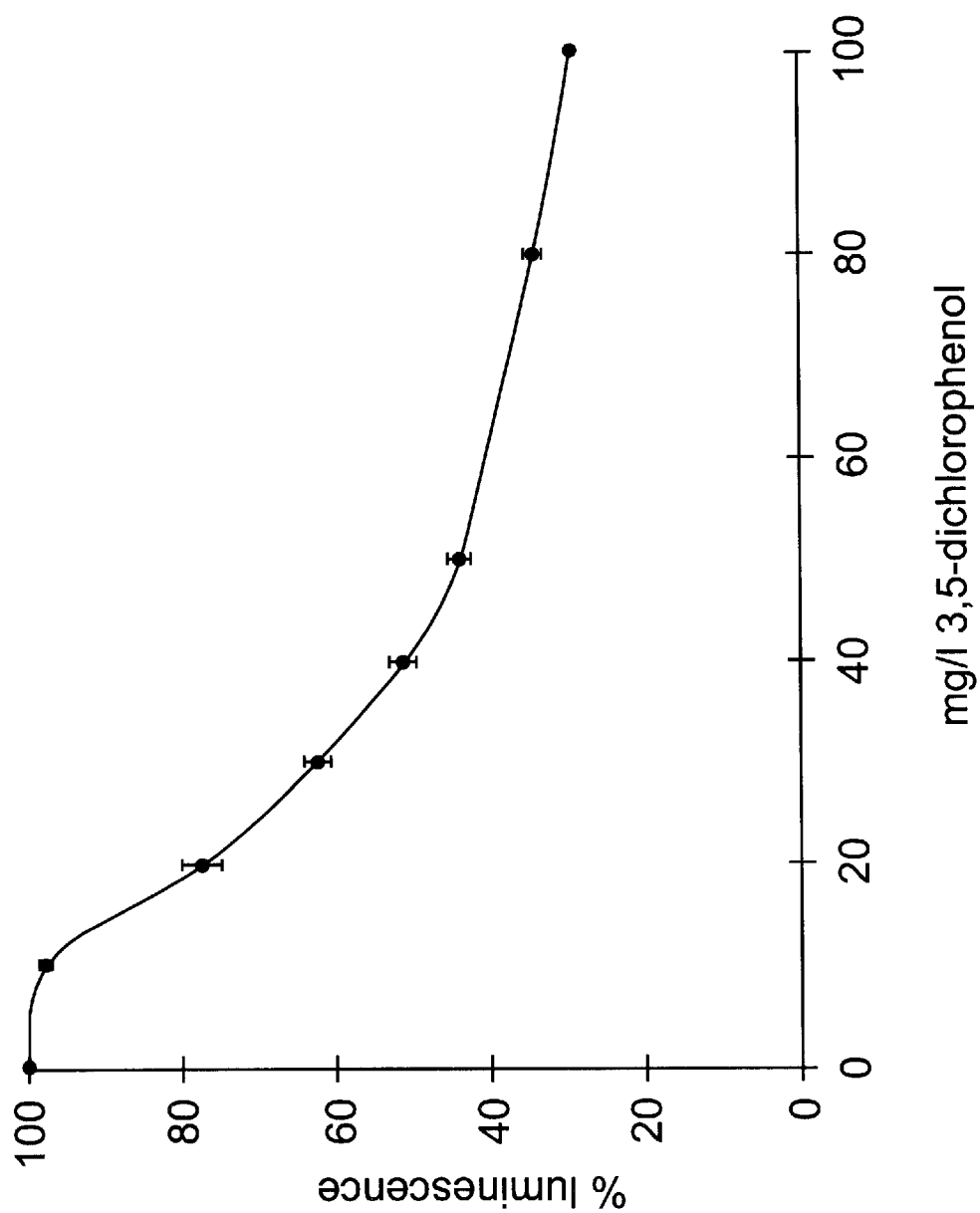

FIG. 6 is a graphical representation of the luminescence of the S. cerevisiae pPLUCΔP biosensor 10 minutes after exposure to a range of 3,5-dichlorophenol concentrations.

Figure 7:
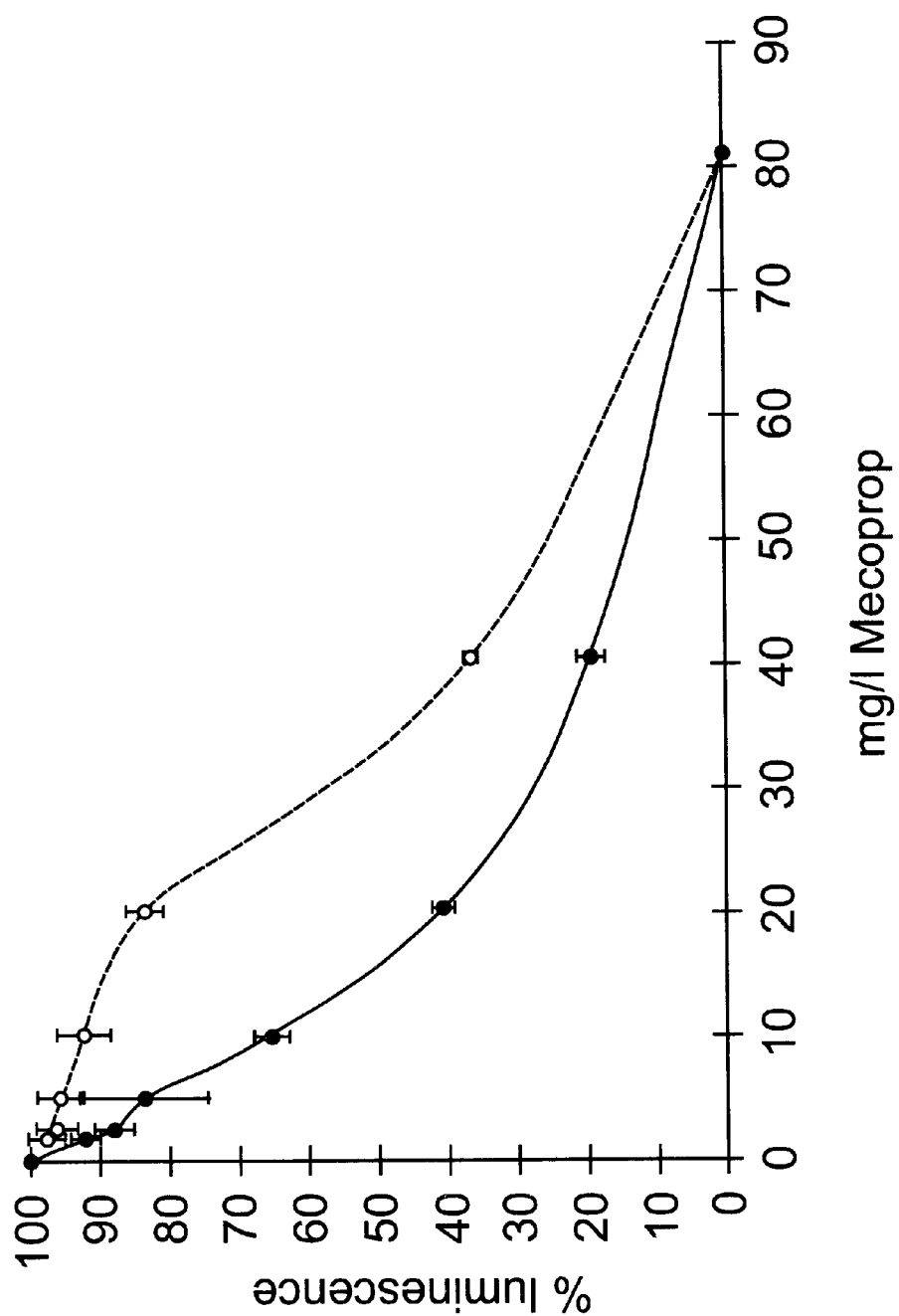

FIG. 7 is a graphical representation of the luminescence of the S. cerevisiae pPLUCΔP biosensor

——•—— compared with the luminescence of a E. coli biosensor

----O----

10 minutes after exposure to a range of MECOPROP® concentrations.

Figure 8:
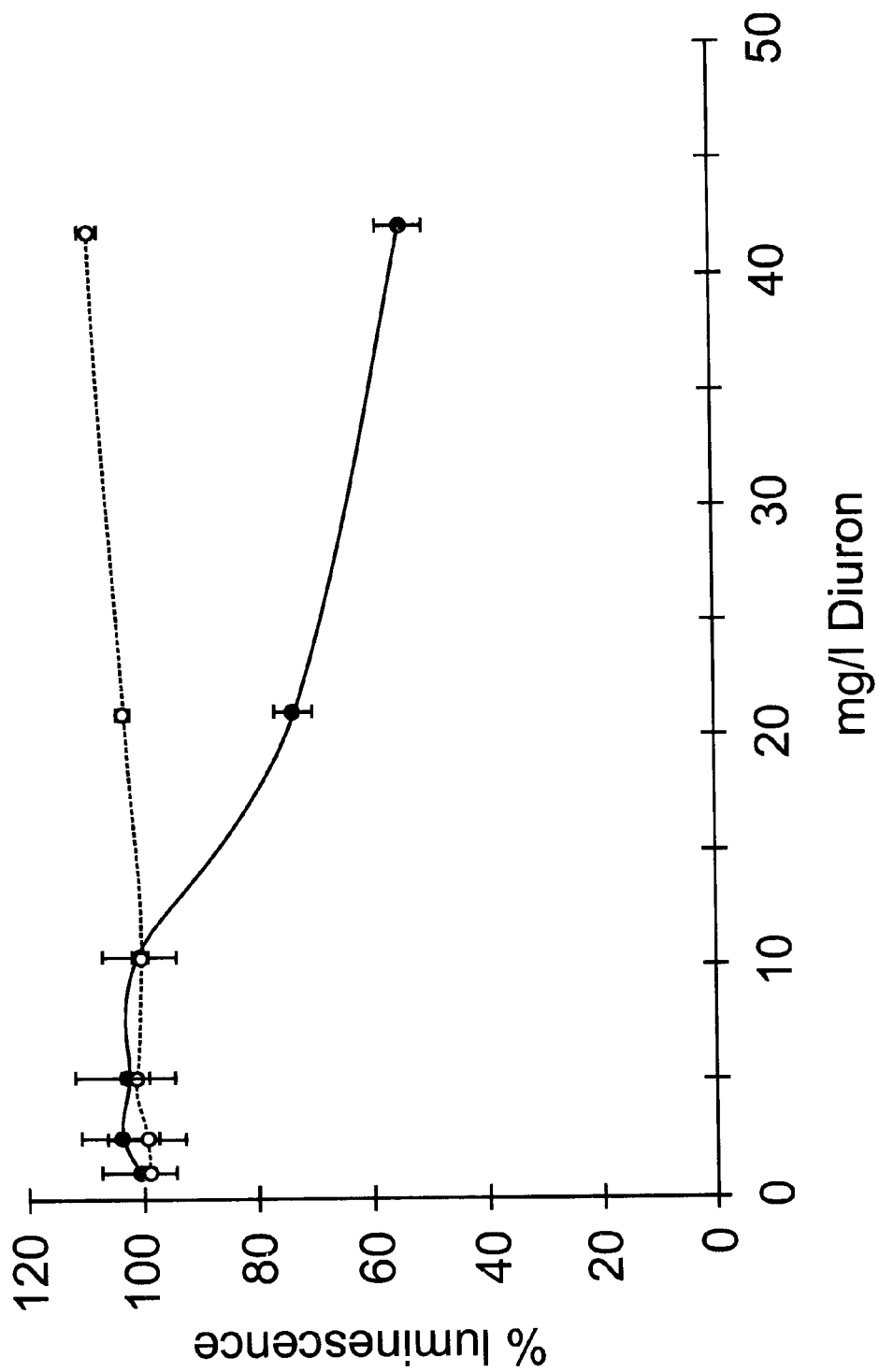

FIG. 8 is a graphical representation of the luminescence of the S. cerevisiae pPLUCΔP biosensor

——•—— compared with the luminescence of the E. coli biosensor

----O----

10 minutes after exposure to a range of DIURON® concentrations.

Figure 9:
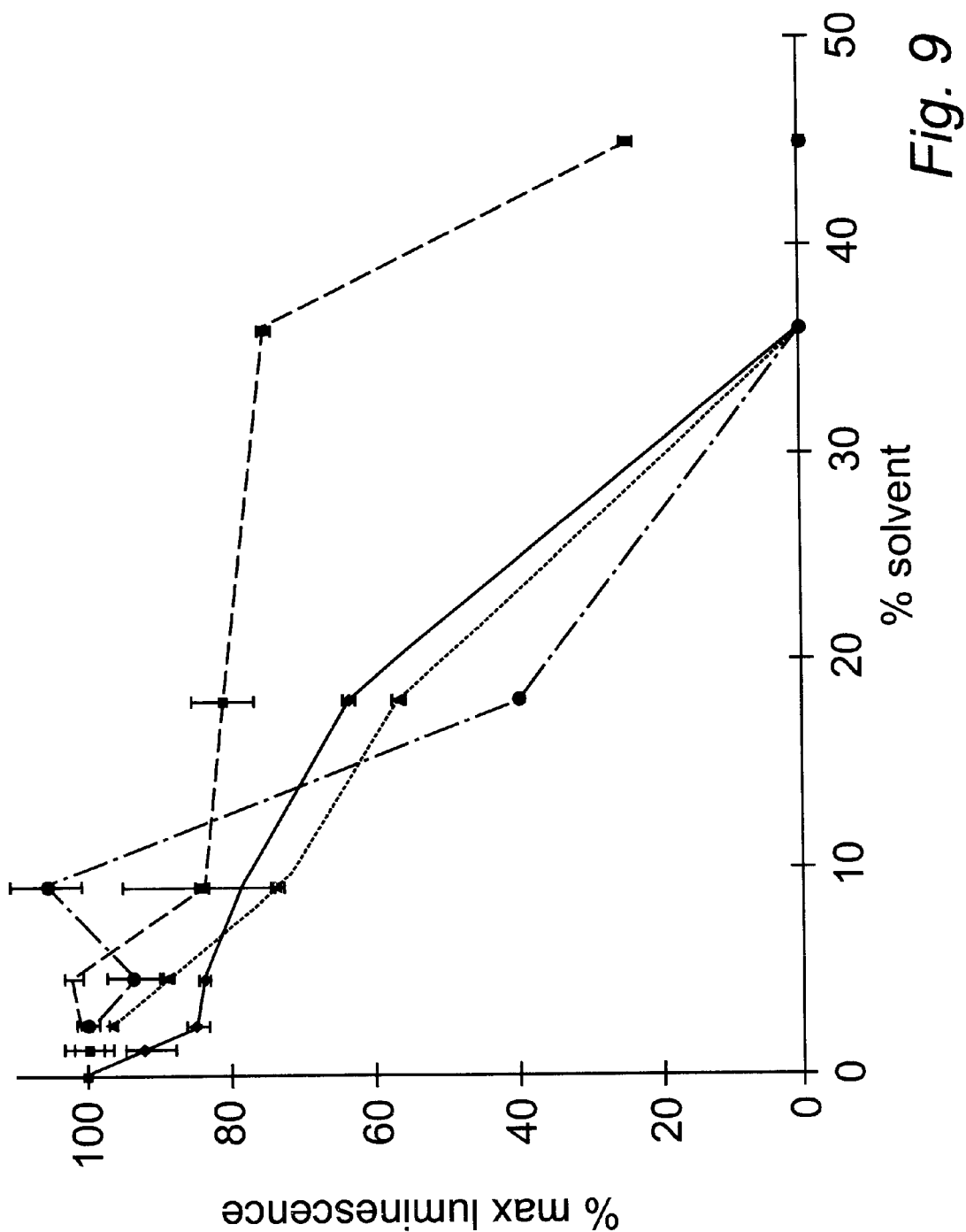

FIG. 9 is a graphical representation of the effect on the luminescence of the S. cerevisiae pPLUCΔP when placed in a range of concentrations; ethanol (——♦——)

methanol (----5----)

acetone (——1——)

and DMSO (——n——).

Figure 10A:
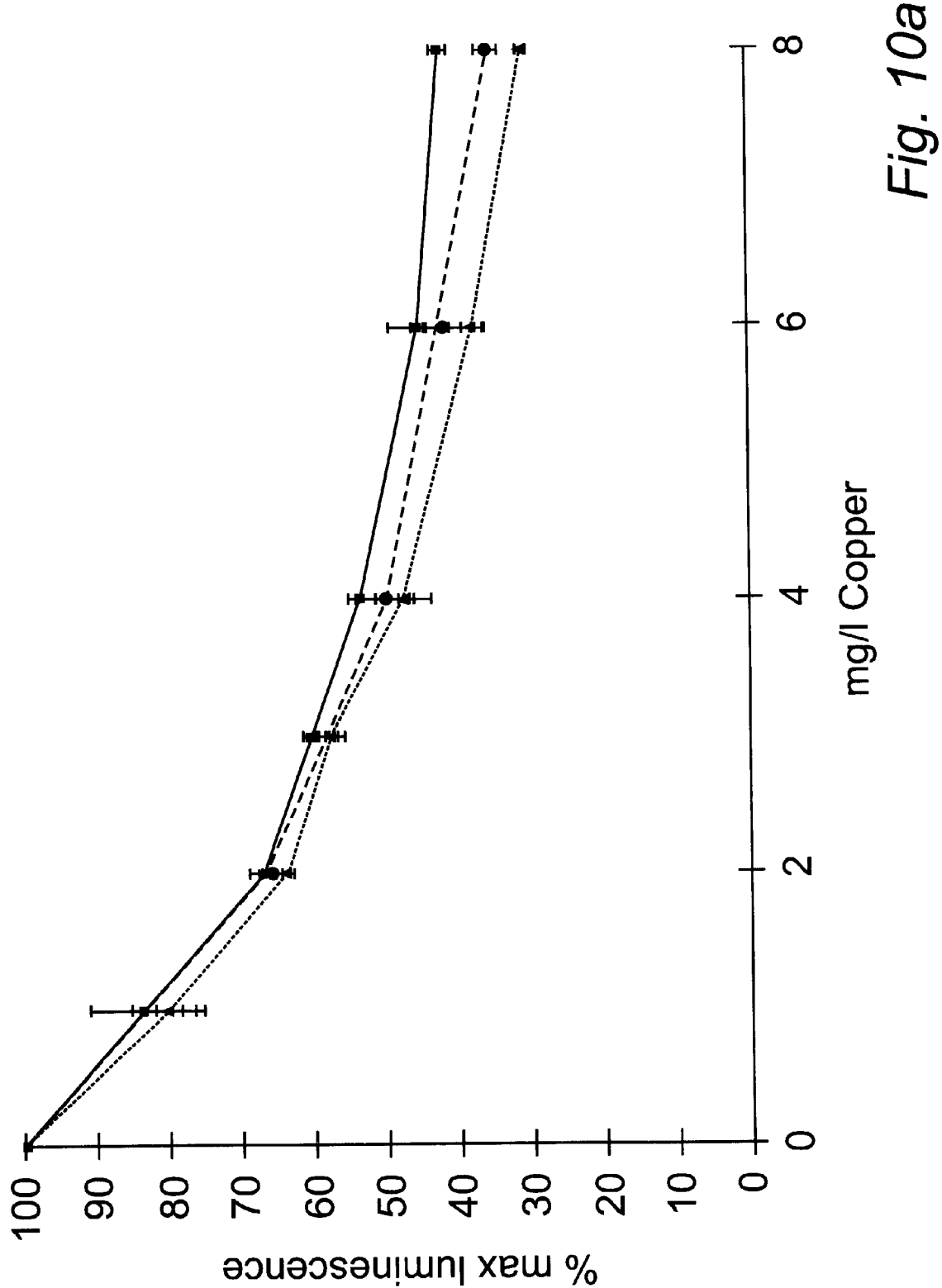

FIG. 10a is a graphical representation of the effect of varying the amount of time the S. cerevisiae pPLUCΔP biosensor was exposed to varying concentrations of copper. The amount of exposure was either 5 mins (——n——), 10 mins (----5----)

or 15 mins (——1——).

FIG. 10b is a graphical representation of the effect of varying the amount of time the S. cerevisiae pPLUCΔP biosensor was exposed to varying concentrations of copper. The amount of exposure was either 10 mins

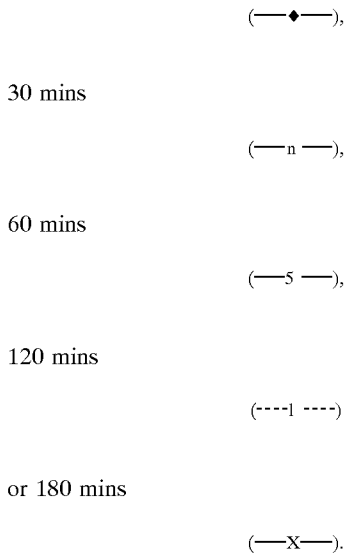

30 mins (—♦—), 60 mins (—п—), 120 mins (—5—), or 180 mins (----1----)

(—x—).

Figure 11:
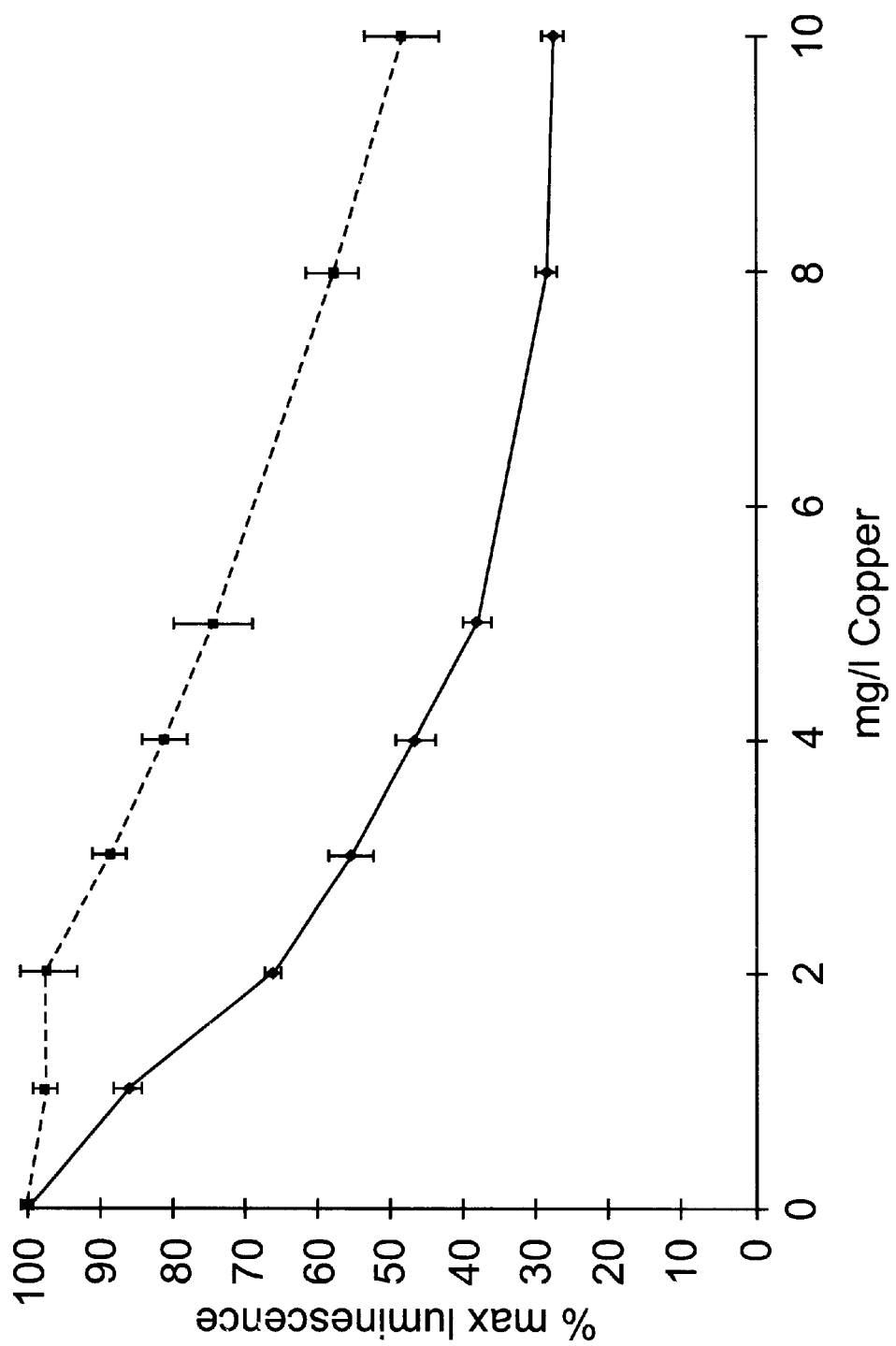

FIG. 11 is a graphical representation of the stability of the S. cerevisiae LUCΔ biosensor. The amount of exposure to copper was 10 mins. The sensor cells were either used for the assay after 10 mins.

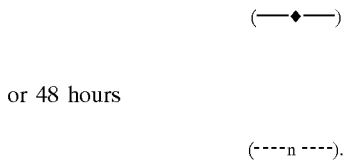

(—♦—)

or 48 hours (----п----).

Figure 12:
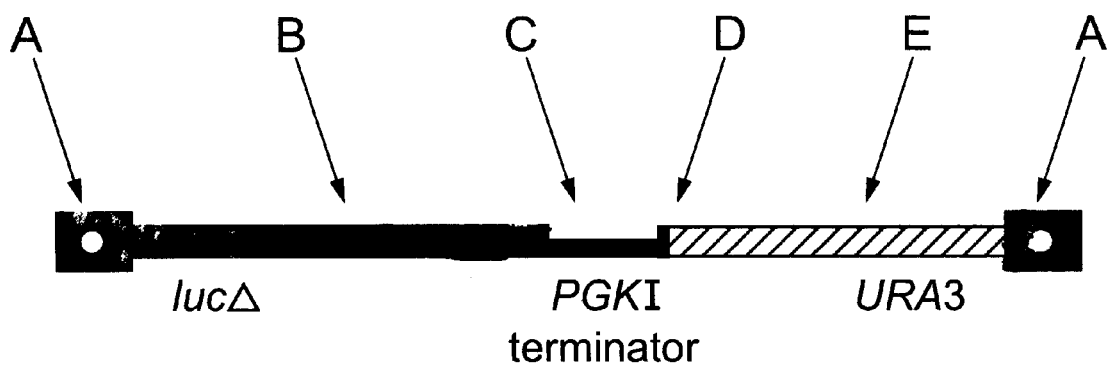

FIG. 12 shows the rps16A gene disruption cassette used in LucΔ strain constructs containing the modified luciferase reporter gene with PGK terminator and urs3 selective marker. Region A is the region which is homologous with the rps16A gene; Region B is the luciferase gene; Region C is the $PGK_{term}$; Region D is the common region of homology; Region E is the URA3 gene.

Figure 13:
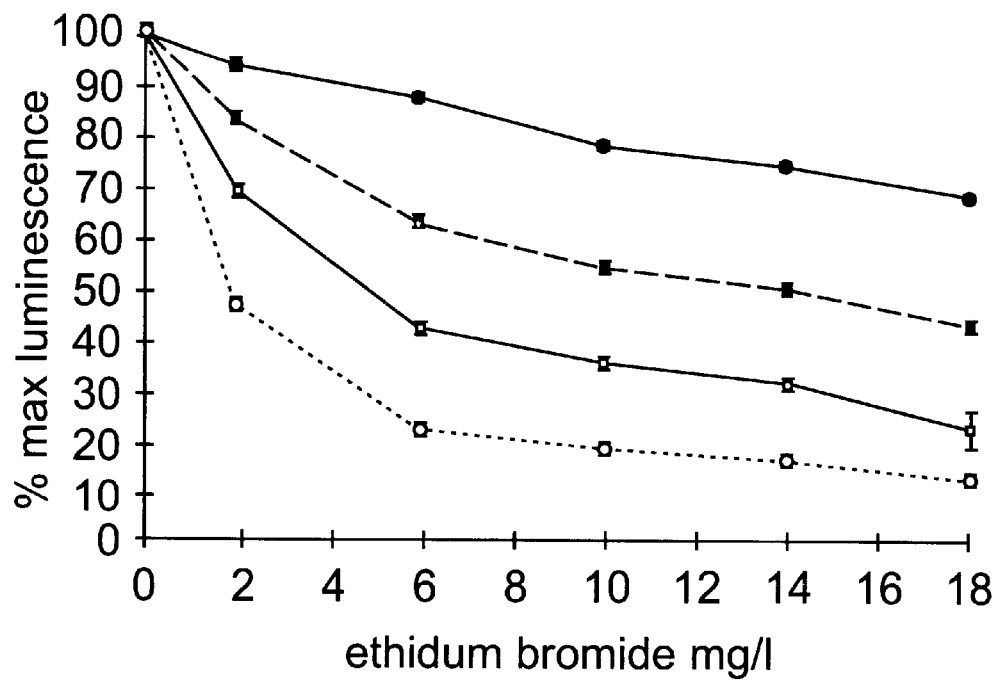
Figure 14:
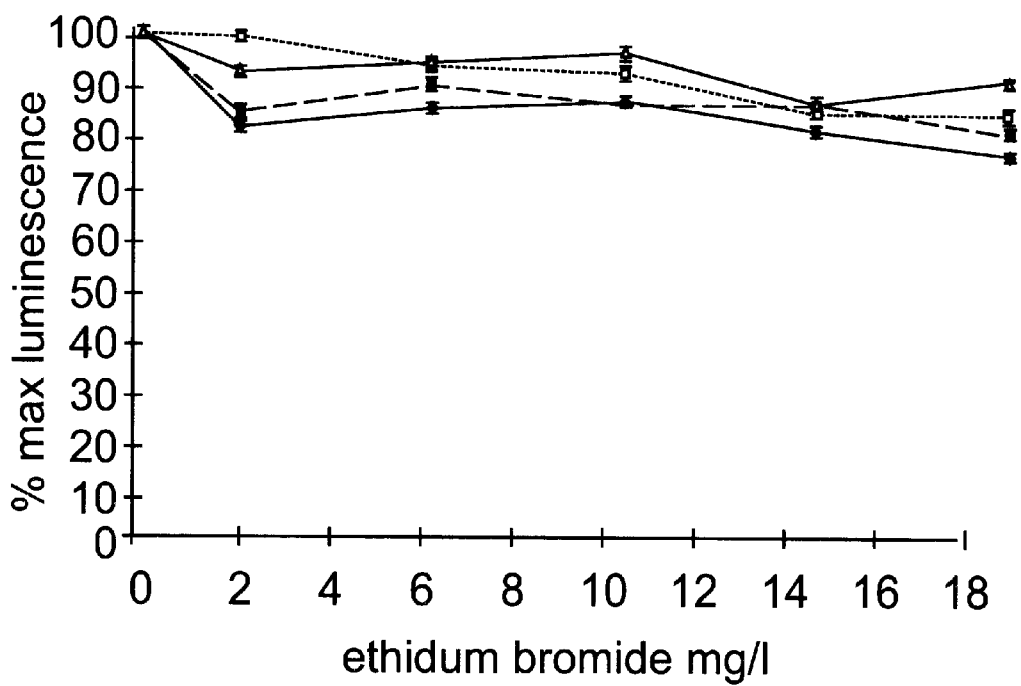

FIG. 13 shows graphically the effect of ethidium bromide on non-dividing S. cerevisiae cells; and FIG. 14 shows graphically the effect of ethidium bromide on dividing S. cerevisiae cells.

EXAMPLE 1

Production of a S. cerevisiae Biosensor

Figure 1A:
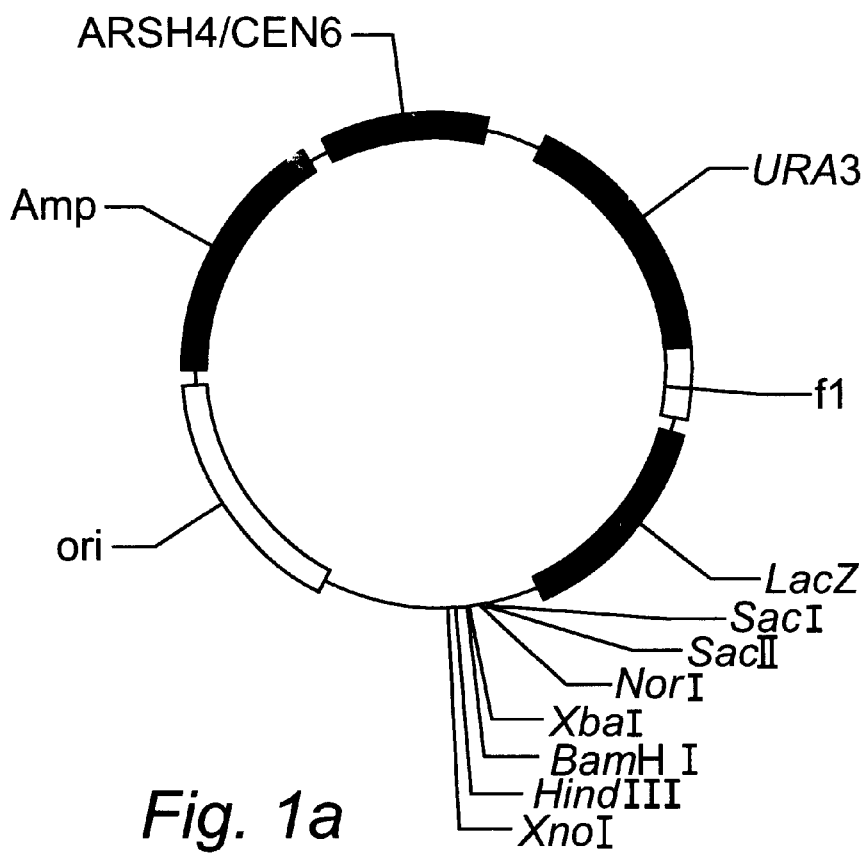
FIG. 1a shows a diagram of a centromeric shuttle vector pRS316 which is used to produce a biosensor plasmid.

A pBLUESCRIPT® based yeast centromeric plasmid pRS316 (FIG. 1a) with a GAL1 promoter was used as the vector for a luciferase gene. A PGK terminator region was added to the luciferase gene by amplification with primers, designed to introduce restriction enzyme sites to place the terminator at the 3' end of the polylinker using PCR. A SacII site included in the primer S5R (FIG. 2a) at the 5' end and a SacI site included in the primer S3R (FIG. 2a) at the 3' end of this region allowed directional cloning of the PGK terminator.

Figure 1B:
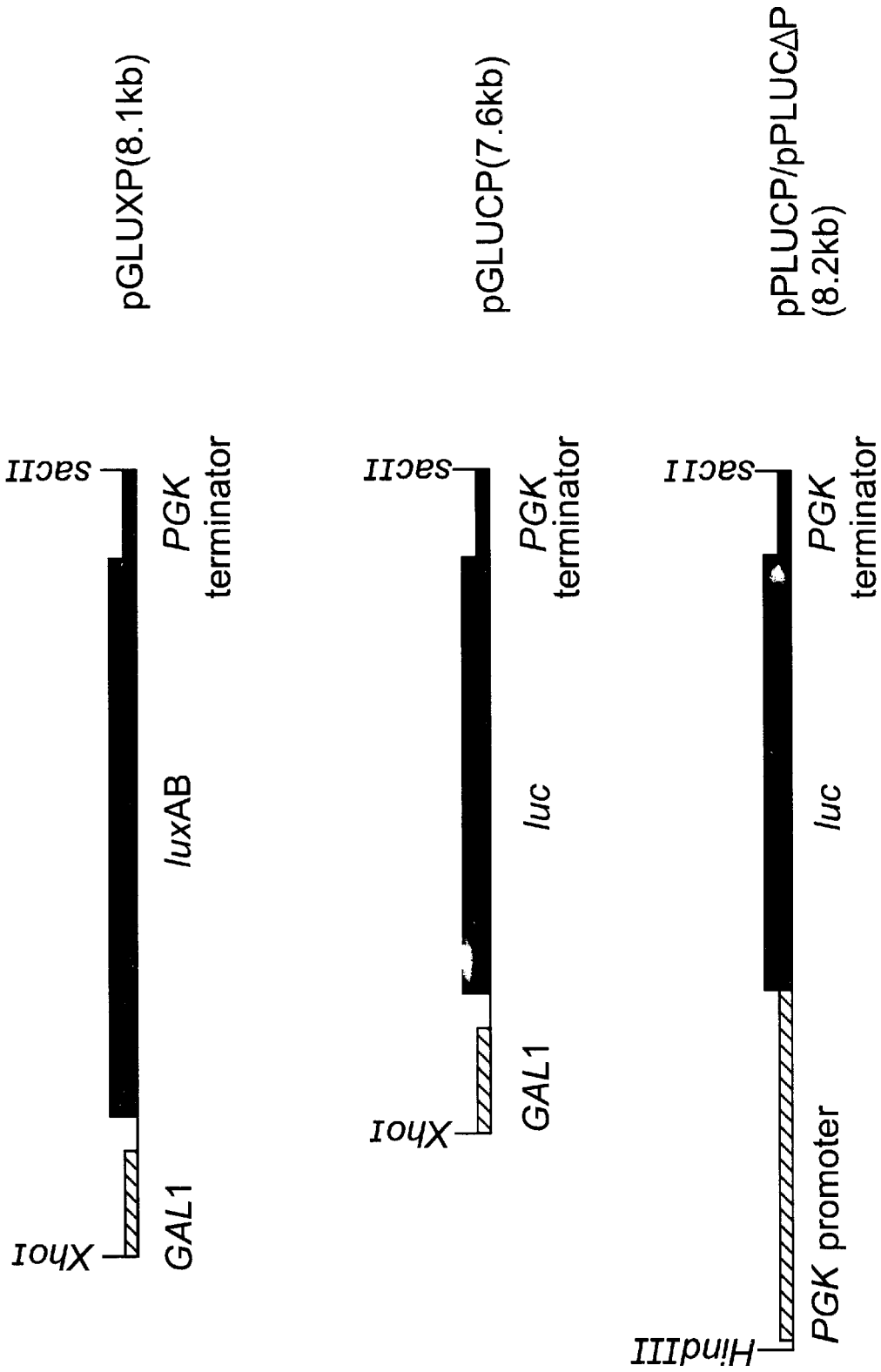
FIG. 1b shows a diagram of luciferase expression cassette which have been inserted into relevant restriction sites of the vector pRS316.

Four different luciferase expression cassettes were produced and placed into the vector to produce four different biosensors; one using a bacterial luciferase from Vibrio harveyi (pGLUXP) and three using a eukaryotic luciferase from Photinus pyralis which is a firefly luciferase (pGLUCP and pPLUCΔP) (FIG. 1b).

The pGLUXP vector was constructed by the addition of a 2.16 kb fused luxAB gene (see Boylan M, et al., Journal of Biological Chemistry, 264 pp 1915 to 1918, 1989) that had been amplified as above to include directional cloning sites into the vector pRS316. A XbaI site introduced by X5R (FIG. 2a) to the 5' end of the gene and a NotI site introduced by N3R (FIG. 2a) at the 3' end of the luxAB fusion ensures that the gene would be inserted in the correct orientation with respect to the promoter and terminator regions.

The pGLUCP vector was constructed by the addition of a 1.65 kb eukaryotic luciferase gene, luc, into the polylinker between the GAL1 promoter and PGK terminator. Again PCR mutagenesis was undertaken to add a BamHI site 5' to the gene using the primer B5RL (FIG. 2a) and a NotI site 3' of the luciferase using the primer N3RL. The template used for this PCR reaction was the pGL2 vector from Promega.

The pPLUCP vector was constructed by replacing the GAL1 promoter in the polylinker with a PGK1 promoter. The luciferase gene, luc, in pPLUCP was modified to include an optimised 5' leader sequence using the primer 5LEADL (FIG. 2a). The PCR reaction for amplifying the luciferase gene with 5LEADL includes the primer N3RL for the inclusion of a NotI site 3' to the luciferase gene.

The pPLUCΔP vector was carried by inserting luc, amplified using the primers 5LEADL and N3RD (FIG. 2a) which removes the 9 bp carboxyl terminal peroxisome targeting sequence of the luciferase gene, into the vector pRS316. The 1.65 kb lucΔ produced from the PCR reaction is inserted into the vector in the same restriction sites used for pPLUCP.

Each vector was then inserted in to the S. cerevisiae using standard transformation procedures.

Bioluminescence was monitored using Bio-Orbit 1251 luminometer connected to a Multiuse software package. The units of luminescence were expressed as RLU (relative light units) which equate to 10 $mVs^{-1}ml^{-1}$.

In vivo luciferase activity assays using S. cerevisiae require acidification to allow the substrate for the light reaction (luciferin) to freely enter intact cells. Therefore, a two-step assay procedure was designed to incorporate separate toxicity analysis without pH adjustment and subsequent acidification for luminescence quantification. In preparation for the assay, S. cerevisiae cells were harvested at peak luminescence (around 3 to $4 \times 10^8$ cells/ml), centrifuged at 700 g (3000 rpm) and washed twice in 5 mM KCl; keeping the original volume constant for the first wash, but halved for second wash (allowing for modified dilution in assay). The first step (exposure), 50 μl of washed S. cerevisiae cells are added to a 450 μl sample (pH generally not important). In an alternative procedure the S. cerevisiae can also be resuspended in water rather than in 5 mM Kcl. The second step (acificiation), 500 μl citrate phosphate buffer (pH2.5), also containing the luciferan (0.1 mM final concentration in 1 ml sample), are added to make up 1 ml total volume for subsequent luminescence quantification. The exposure time is generally 10 minutes, but this can be lengthened or shortened depending on assay requirements (e.g. FIGS. 10a, 10b and 11). The assay allows for the full pH durability of S. cerevisiae to be exploited as prior pH adjustment of samples is not required. Luminescence of the sample containing cuvettes are compared to a blank containing diluent (s) used in the assay. This blank defines 100% luminescence.

For bioluminescence monitoring during growth using S. cerevisiae with vector pGLUXP, 5 μl of 100% n-decyl aldehyde was added to the culture in each 1 ml luminometer cuvette. In assays using S. cerevisiae with each of the vectors pGLUCP, pPLUCP and pPLUCΔP, 5 μl of 20 mM of luciferin dissolved in MilliQ deionised $H_2O$ was added to the culture in each 1 ml luminometer cuvette. If caged luciferin was used 1 $\mu$l of 200 mM DMNPE "caged" luciferin was used instead of the 5 $\mu$l free luciferin. All assays were performed at 25° C.

As can be seen from FIG. 11 *S. cerevisiae* pPLUCΔP biosensor luminesces for more than 48 hours.

In order to assess the pH tolerance of the biosensor, deionised water had its pH adjusted with HCl and NaOH to a point in the range of pH1 to pH12. The *S. cerevisiae* cells were harvested at peak luminescence, centrifuged at 700 g and washed twice in 10 mM KCl; keeping the original volume constant. pH adjusted deionised water (450 $\mu$l) was added to each cuvette. The volume was made up to 500 ml using 3 to 4×10$^7$ cells. Bioluminescence was then monitored following a 10 minute exposure to the sample, and the subsequent addition of citrate/phosphate buffer (pH 2.5) containing 0.1 mM luciferin.

Stock concentrations of the toxicants (copper, 3,5-dichlorophenol, MECOPROP® and DIURON®) were made in deionised water and their pH adjusted to 5.5 using HCl and NaOH. Dilutions were then made of the stock solutions using deionised water adjusted to pH5.5, as above. The cells were harvested at peak luminescence, centrifuged at 700 g and washed twice in 5 M KCl; keeping the original volume constant. The toxicant (450 $\mu$l) was added to each cuvette. The final volume was then made up to 500 $\mu$l using 3 to 4×10$^7$ cells. After 10 min, 500 $\mu$l of citrate phosphate buffer (pH 2.5) containing 5 $\mu$l of 20 mM luciferin was added to each cuvette and the bioluminescence was monitored.

The results shown in FIGS. 5 and 6 show that the transformed *S. cerevisiae* pPLUCΔP biosensor can detect both inorganic (copper) and organic (3,5-dichlorophenol) toxic substances and as shown in FIGS. 10a, 10b the *S. cerevisiae* pPLUCΔP biosensor can serve as an acute (up to 15 minutes exposure to sample) and as a chronic (up to 180 minutes exposure to the sample) biosensor. FIG. 11 shows that the biosensor is still actively detecting copper after 48 hours growth.

A direct composition of light output from the *P. pyralis* and fused *V. harveyi* luciferases were undertaken through placing the luciferase genes in the same GAL1/PGK1 expression system. Expression of the fused bacterial luciferase resulted in a low light output per milliliter of culture. Expression of the eukaryotic lucerifase produced far higher light output (around 100 fold) and as a result was selected for use in the final biosensor construct. The PGK1 promoter was chosen as it has efficacious properties, such as high levels of expression and no requirement for medium change when inducing expression. It was also found that light output from the PGK1 containing constructs was around 10 to 20 fold higher than GAL1 containing constructs.

Final modifications of the biosensor construct were made to the luciferase gene itself when 9 bp from the carboxyl terminal was removed using PCR mutagenesis. This adjustment removed a peroxisome targeting sequence which prevents targeting of the lucerifase to the peroxisome. This strain, pPLUCΔP, was further characterized and applied in toxicity analysis.

Figure 3:
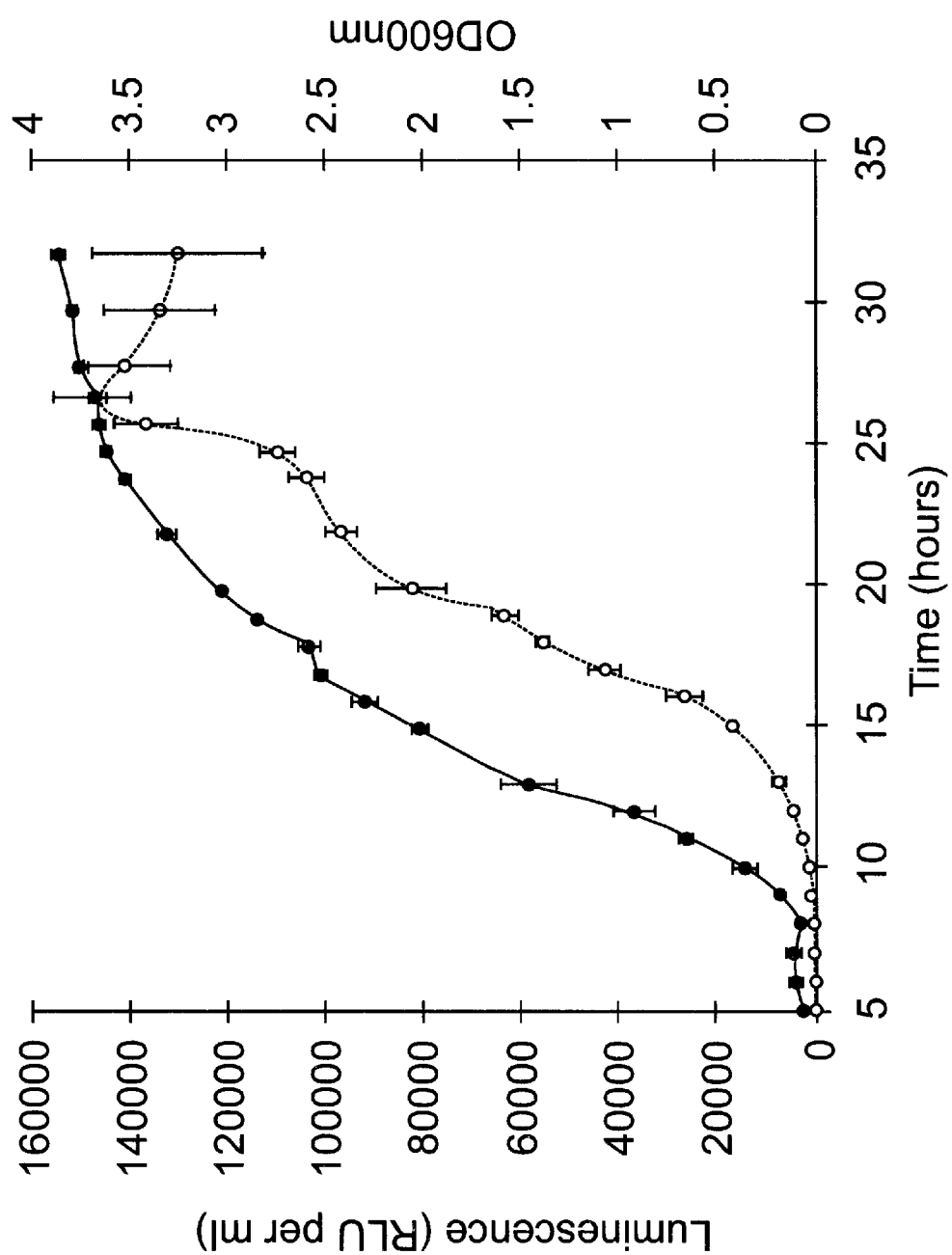
FIG. 3 is a graphical representation of the luminescence of S. cerevisiae pPLUCΔP after transformation with the biosensor plasmid. The mean RLU (Relative Light Units)

Growth of *S. cerevisiae* containing pPLUCΔP was monitored and the results are shown in FIG. 3. Following inoculation light output increased with cell numbers and reached a peak output after 27 hours, as cells entered stationary phase. Cells were harvested at this point, when $OD_{600 nm}$ was around 3.65. It was observed that the luminescence after this time declines slowly, which is dissimilar to the situation for bacteria. Bacterial biosensors constitutively expressing luciferase lose luminescence rapidly as the cells enter stationary phase, whereas the *S. cerevisiae* biosensor maintains bioluminescence into the stationary phase and still functions as a biosensor (FIG. 11).

Assays were carried out to discover if there were differences between sensing capabilities of the new *S. cerevisiae* biosensor and an existing *E. coli* biosensor. Results are displayed graphically for MECOPROP® and DIURON® in FIGS. 7 and 8 respectively. The dose response curves obtained for the herbicides MECOPROP® and DIURON® indicate that the *S. cerevisiae* is more sensitive in toxicity assays for these compounds. MECOPROP® was detected at levels far lower than *E. coli* could sense (twice as sensitive). In contrast to the *S. cerevisiae* pPLUCΔP biosensor DIURON® toxicity was not observed at all when assaying toxicity using the *E. coli* biosensor at the concentrations tested.

In order to assess the solvent tolerance of the biosensor; methanol, ethanol, acetone and DMSO dilutions were prepared for analysis. Dilutions ranging from 1% to 50% were made. The *S. cerevisiae* cells were harvested at peak luminescence, centrifuged at 700 g and washed twice in 10 mM KCl; keeping the original volume constant for the first wash, but halved for second wash. 450 $\mu$l of the solvent dilutions was added to the respective cuvettes. 50 $\mu$l of *S. cerevisiae* cells were then added to each cuvette. Simulations acidification and substrate addition was carried out after a 10 minute exposure. Luminescence was then quantified. Results shown in FIG. 9.

EXAMPLE 2

Production of a *S. cerevisiae* Biosensor with no Antibiotic Resistance Gene Luciferase and ura3 genes from the vector pPLUCΔP were separated from the plasmid using PCR. The ST1K1 primer (see FIG. 2b) was designed so that the ura3 gene would be modified to allow the joining of the luciferase gene in a 5' position and the ura3 gene in a 3' position to form the integrating expression cassette (see FIG. 12) in a subsequent PCR (discussed below). The primers were also designed so that the whole cassette should be targeted to a duplicated constitutively expressed ribosomal gene rps16a in the *S. cerevisiae* genome. The primers rLUC and S3R (see FIGS. 2a and b) were used to amplify a promoterless luciferase gene including the PGK terminator region and the addition of a 50 bp homology region to rps16a promoter for integration included in rLUC primer. The primers rURA and ST1K1 (see FIG. 2b) were used to amplify the ura3 gene including all of its control regions (promoter and terminator) and the additional regions for genomic integration included in rURA and homology to the previously produced luciferase amplification product included in ST1K1. The common homology allows an overlap of 20 bp between the 3' end of the rLUC/S3R and 5' end of the ST1K1/rURA PCR products. These two products were then added together in a final PCR reaction to allow fusion of the luciferase and ura3 genes through this homology and amplification of the resultant 3.5 kb product. The primers mrL and mrU (see FIG. 3b) are homologous to sections of the rps16a regions introduced by the rLUC and rURA primers respectively. Therefore, allowing amplification of the 3.5 kb product with the ribosomal flanking regions.

The fragment was then purified (gel electrophoresis) and concentrated for transformation of *S. cerevisiae* (Gietz R.

D.; Schiosh, R. H.; Willems. A. R. and Woods, R. A. 1995, Studies on the transformation of intact yeast cells by the LiAc/SDNA/PEG procedure:-Yeast 11, 355–60). Very few colonies are obtained, e.g. 100 to 1000 fold less than can be expected if transforming with a plasmid, as you are relying on a spontaneous event.

The *S. cerevisiae* biosensors of the Examples 1 and 2 have all the advantages of the prokaryotic systems, including rapid and cheap quantification of toxicity. Additionally, their wide range pH tolerance allows toxicity and bioavailability analysis to be carried out from at least pH 1 through pH 12. The lucΔ construct in Example 2 does not contain antibiotic resistance genes and the organism itself is not a known pathogen, therefore having minimal disadvantages for field use. Most importantly, *S. cerevisiae* is a eukaryotic organism that is sensing different xenobiotics at different concentrations compared to bacterial biosensors. This *S. cerevisiae* biosensor may not just revolutionise environmental monitoring as the pharmaceutical industry would be also benefit by this system as it is able to provide rapid and cheap preliminary screens for in vivo toxicity to a eukaryotic cell.

The biosensors are stable over a prolonged period (at least 48 hours) so that as a biosensor reagent it is a particularly suited for on-line applications.

EXAMPLE 3

Dividing Cell Assays

The following procedure was designed to monitor the effect of increasing the exposure time up to 9 hours and to determine the different responses of dividing and non-dividing biosensor cells to the presence of DNA-damaging agents. For assay preparation, the diluent used was ethanol at 4.5% final concentration. All ethidium bromide dilution standards were prepared in glassware. Cells for the dividing assays were only pelleted once at 700× G for 1 minute before resuspension in 10× SC (-ura) medium (Strathern, J. N. (1994) Ty Insertional mutagenesis. In: Johnston, J. R. [Ed] *Molecular genetics of yeast; a practical approach*, pp. 118 [Oxford University press]) for the dividing cultures (to give a 1× SC (-ura) final concentration. Cells for the non-dividing assay were harvested at 700× G for 1 minute and washed twice in deionised water. The different cell resuspensions for dividing and non-dividing protocols were assayed with duplicated standards for toxicity analysis. Assays were performed in 96 well plates adding 10 μl cells (around 4×10$^6$ cells) to 90 μl standard. The black 96-well plates were covered with a plate sealer and incubated at 30° C. before and between readings. The exposure times were 3, 5 h, 7 h, and 9 h. Additional of 100 μl citrate phosphate buffer (pH 2.5), containing 0.2 mM luciferin, was performed at each time point before luminescence quantification in a Lucy Anthos 1 luminometer using the *Stingray* (v2.0b31) software package. Following luminescence quantification 100 μl was removed from the blank well in the dividing assays for $OD_{600}$ measurements and cell counts. This was performed at each time point to ensure cell division was or was not occurring inn the dividing and non-dividing assays respectively.

The results of the dividing and non-dividing assays are shown in FIGS. 13 and 14 respectively.

Thus in FIG. 13, the effect of ethidium bromide on dividing cells was measured by recording luciferase activity from cells in wells containing ethidium bromide dilutions prepared in 4.5% ethanol. The cells were capable of division as they were resuspended in a 1× SC (-ura) final concentration. A clear decrease in cell division with increasing ethidium bromide concentration with time was observed (3 h (•), 5 h (■), 7 h (Δ), 9 h (□)). These results were obtained with the LucΔ *S. cerevisiae* strain in 96-well plates using the Lucy Anthos 1 luminometer. The experiment was carried out in triplicate at 25° C. and the error bars represent standard errors of the mean triplicate value.

In FIG. 14, the effect of ethidium bromide on non-dividing cells was measured by recording the light output from cells in wells containing ethidium bromide dilutions prepared in 4.5% ethanol. The cells were incapable of division as they were resuspended in pure ddH$_2$O. The response of the cells to ethidium bromide does not change with increased exposure time (3 h (•), 5 h (■), 7 h (Δ), 9 h (□)). There was no clear toxic effect in these non-dividing cells, compared to the situation with dividing cells illustrated in FIG. 13. These results were obtained with the LucΔ *S. cerevisiae* strain in 96-well plates using the Lucy Anthos 1 luminometer. The experiment was carried out in triplicate at 25° C. and the error bars represent standard errors of the mean triplicate value.

What is claimed is:

1. A method for evaluating a biological effect of a substance, the method comprising:
   preparing a eukaryotic biosensor engineered with a gene which constitutively expresses a light emitting protein;
   sampling the substance;
   subjecting the sampled substance at a pH between pH1 and pH12 to an assay in the presence of the biosensor; and
   monitoring changes in light output.

2. The method according to claim 1, wherein the eukaryotic biosensor is derived from Saccharomyces genus.

3. The method according to claim 2, wherein the eukaryotic biosensor is derived from *Saccharomyces cerevisiae*.

4. The method according to claim 1, wherein the light emitting protein is a luciferase.

5. The method according to claim 4, wherein the luciferase is either a bacterial luciferase or a eukaryotic luciferase.

6. The method according to claim 5, wherein the bacterial luciferase is from *Vibrio harveyi*.

7. The method according to claim 5, wherein the eukaryotic luciferase is from *Photinus pyralis*.

8. The method of claim 1, wherein the substance is contaminated with a xenobiotic compound.

9. The method according to claim 8, wherein the xenobiotic is selected from the group consisting of copper, 3,5-dichlorophenol, 2,4-dichlorophenol, (±)-2-(4-chloro-0-tolyloxy)propionic acid, 3-(3,4-dichlorophenyl)-1,1-dimethylurea, paralytic shellfish toxins, benzo (a) pyrene, and MCPA.

10. The method according to claim 1, wherein the substance is contaminated with a bioactive compound.

11. The method according to claim 1, wherein the substance is contaminated with an organic solvent.

12. The method according to claim 11, wherein the organic solvent is selected from the group consisting of ethanol, methanol, acetone, and DMSO.

13. The method according to claim 1, wherein the eukaryotic biosensor undergoes cell division during the assay.

14. The method according to claim 1, wherein the substance is a potable water.

15. The method according to claim 1, wherein the assay comprises luciferin.

16. The method according to claim 1, wherein the assay further comprises altering the pH of the admixture of the substance and the biosensor to pH5.5.

17. A biosensor comprising a eukaryotic bioengineered organism with a chromosomally integrated gene fragment that constitutively expresses a light emitting protein and which is capable of emitting varying levels of light according to an environmental condition surrounding the organism.

18. The biosensor according to claim 17, wherein the bioengineered organism is derived from Saccharomyces genus.

19. The biosensor according to claim 18, wherein the bioengineered organism is derived from *Saccharomyces cerevisiae*.

20. The biosensor according to claim 17, wherein the organism is stable at a pH between pH 1 and pH 12.

21. The biosensor according to claim 17, wherein the light emitting protein is a luciferase.

22. The biosensor according to claim 21, wherein the luciferase is either a bacterial luciferase or a eukaryotic luciferase.

23. The biosensor according to claim 22, wherein the bacterial luciferase is derived from *Vibrio harveyi*.

24. The biosensor according to claim 22, wherein the eukaryotic luciferase is derived from *Photinus pyralis*.

25. The biosensor according to claim 17, wherein the bioengineered organism is stable in an organic solvent having a concentration of up to 10% (v/v).

26. The biosensor according to claim 25, wherein the organic solvent is selected from the group consisting of ethanol, methanol, acetone, and DMSO.

27. The biosensor according to claim 17, wherein said biosensor is reagent stable for at least 48 hours.

28. The method according to claim 17, wherein the eukaryotic biosensor undergoes cell division during the assay.

29. A eukaryotic biosensor *S. cerevisiae* pPLUCΔp deposited in the National Collection of Industrial and Marine Bacteria on the Aug. 28, 1998 under number NCIMB 40969.

* * * * *

SEQUENCE LISTING

<160> NUMBER OF SEQ ID NOS:    13

<210> SEQ ID NO 1
<211> LENGTH: 87
<212> TYPE: DNA
<213> ORGANISM: Artificial
<220> FEATURE:
<223> OTHER INFORMATION: Description of Artificial  Sequence: Primer

<400> SEQUENCE: 1
acagatcacc ggatccatca agacaccaat caaaacaaat aaaacatcat c acaatggaa      60 gacgccaaaa acataaagaa aggcccg                                          87

<210> SEQ ID NO 2
<211> LENGTH: 36
<212> TYPE: DNA
<213> ORGANISM: Artificial

```
<220> FEATURE:
<223> OTHER INFORMATION: Description of Artificial   Sequence: Primer

<400> SEQUENCE: 2
tttgcaaaaa gcttgggatc ccggtactgt tggtaa                           36

<210> SEQ ID NO 3
<211> LENGTH: 18
<212> TYPE: DNA
<213> ORGANISM: Artificial
<220> FEATURE:
<223> OTHER INFORMATION: Description of Artificial   Sequence: Primer

<400> SEQUENCE: 3
agcctcataa ataaaggt                                               18

<210> SEQ ID NO 4
<211> LENGTH: 18
<212> TYPE: DNA
<213> ORGANISM: Artificial
<220> FEATURE:
<223> OTHER INFORMATION: Description of Artificial   Sequence: Primer

<400> SEQUENCE: 4
ttttctcctt acgcatct                                               18

<210> SEQ ID NO 5
<211> LENGTH: 36
<212> TYPE: DNA
<213> ORGANISM: Artificial
<220> FEATURE:
<223> OTHER INFORMATION: Description of Artificial   Sequence: Primer

<400> SEQUENCE: 5 aagggcatc gcggccgctt cagcatcagt taaacg                            36

<210> SEQ ID NO 6
<211> LENGTH: 55
<212> TYPE: DNA
<213> ORGANISM: Artificial
<220> FEATURE:
<223> OTHER INFORMATION: Description of Artificial   Sequence: Primer

<400> SEQUENCE: 6
tctagagcgg ccgctgaata cagttacatt ttactttccg cccttcttgg c cttt     55

<210> SEQ ID NO 7
<211> LENGTH: 36
<212> TYPE: DNA
<213> ORGANISM: Artificial
<220> FEATURE:
<223> OTHER INFORMATION: Description of Artificial   Sequence: Primer

<400> SEQUENCE: 7
tagctaagaa tttgcgggcc gctgaataca gttaca                           36

<210> SEQ ID NO 8
<211> LENGTH: 84
<212> TYPE: DNA
<213> ORGANISM: Artificial
<220> FEATURE:
<223> OTHER INFORMATION: Description of Artificial   Sequence: Primer

<400> SEQUENCE: 8
agcctcataa ataaaggtag atagtaaagt atacaagaga agaatcccaa g atggaagac   60
```

```
gccaaaaaca taaagaaagg cccg                                              84

<210> SEQ ID NO 9
<211> LENGTH: 84
<212> TYPE: DNA
<213> ORGANISM: Artificial
<220> FEATURE:
<223> OTHER INFORMATION: Description of Artificial  Sequence: Primer

<400> SEQUENCE: 9
atcaaacatc attctgcaga actgaaaaca tacttgaaca cttgggacag c tgacctgat     60 gcggtatttt ctccttacgc atct                                             84

<210> SEQ ID NO 10
<211> LENGTH: 36
<212> TYPE: DNA
<213> ORGANISM: Artificial
<220> FEATURE:
<223> OTHER INFORMATION: Description of Artificial  Sequence: Primer

<400> SEQUENCE: 10
tttttcgaaa cgcagagctc tcgagttatt aaactt                                36

<210> SEQ ID NO 11
<211> LENGTH: 36
<212> TYPE: DNA
<213> ORGANISM: Artificial
<220> FEATURE:
<223> OTHER INFORMATION: Description of Artificial  Sequence: Primer

<400> SEQUENCE: 11
gtgttgcttt cttatccgcg gagaaataaa ttgaat                                36

<210> SEQ ID NO 12
<211> LENGTH: 39
<212> TYPE: DNA
<213> ORGANISM: Artificial
<220> FEATURE:
<223> OTHER INFORMATION: Description of Artificial  Sequence: Primer

<400> SEQUENCE: 12
gagctctgcg tttcgaaaaa ccggagacgg tcacagctt                             39

<210> SEQ ID NO 13
<211> LENGTH: 36
<212> TYPE: DNA
<213> ORGANISM: Artificial
<220> FEATURE:
<223> OTHER INFORMATION: Description of Artificial  Sequence: Primer

<400> SEQUENCE: 13
cgtaatacca acaaatctag aaatgttatg aaattt                                36
```